United States Patent
Friesz et al.

(10) Patent No.: US 8,816,103 B2
(45) Date of Patent: Aug. 26, 2014

(54) PROCESS FOR THE PREPARATION OF DRONEDARONE

(71) Applicant: Sanofi, Paris (FR)

(72) Inventors: Antal Friesz, Budapest (HU); Csaba Huszar, Budapest (HU)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/740,505

(22) Filed: Jan. 14, 2013

(65) Prior Publication Data

US 2013/0131358 A1  May 23, 2013

Related U.S. Application Data

(63) Continuation of application No. PCT/HU2011/000067, filed on Jul. 13, 2011.

(30) Foreign Application Priority Data

Jul. 22, 2010  (HU) .................................... 1000386

(51) Int. Cl.
*C07D 307/80* (2006.01)
*C07D 307/79* (2006.01)

(52) U.S. Cl.
USPC ........................................ 549/468; 549/471

(58) Field of Classification Search
CPC ............................ C07D 307/80; C07D 307/79
USPC ................................................ 549/468, 471
See application file for complete search history.

(56) References Cited

U.S. PATENT DOCUMENTS

| | | | |
|---|---|---|---|
| 5,223,510 A * | 6/1993 | Gubin et al. | 514/299 |
| 6,828,448 B2 | 12/2004 | Fino et al. | |
| 6,846,936 B2 | 1/2005 | Biard | |
| 2006/0287300 A1 * | 12/2006 | Klein et al. | 514/223.2 |
| 2012/0065411 A1 | 3/2012 | Kretzschmar et al. | |
| 2012/0077995 A1 | 3/2012 | Kretzschmar et al. | |
| 2012/0289717 A1 | 11/2012 | Friesz et al. | |
| 2012/0330036 A1 | 12/2012 | Friesz et al. | |
| 2013/0012729 A1 | 1/2013 | Bailly et al. | |

FOREIGN PATENT DOCUMENTS

| | | |
|---|---|---|
| CN | 101838252 | 9/2010 |
| EP | 0471609 | 2/1992 |
| WO | WO 02/48132 | 6/2002 |
| WO | WO 03/040120 | 5/2003 |
| WO | WO 03040120 A1 * | 5/2003 |
| WO | WO 2011099010 A1 * | 8/2011 |
| WO | WO 2012/127173 | 9/2012 |
| WO | WO 2012/131408 | 10/2012 |
| WO | WO 2012/131409 | 10/2012 |
| WO | WO 2012/131410 | 10/2012 |

OTHER PUBLICATIONS

Shridhar, G.S., Synthesis & Biological Activity of Some New 2-[(5-Nitro-2-furyl- and 5-nitro-2-thienyl]-N-arulsulphonamides & 1-[2-_5-Nitro-2-furyl & 5-nitro-2-thienyl]sulphonyl Heterocycles, Indian Journal of Chemistry, vol. 20B, Mar. 1981, pp. 234-237.*
Wuts, G.M., Greene's Protective Groups in Organic Synthesis, Fourth Edition, John Wiley and Sons, Chapter 7, Protection for the Amino Group, pp. 696-926.*
Shridhar, G.S., Synthesis & Biological Activity of Some New 2-[(5-Nitro-2-furyl- and 5-nitro-2-thienyl]-N-arylsulphonamides & 1-[2-5-Nitro-2-furyl & 5-nitro-2-thienyl]sulphonyl Heterocycles, Indian Journal of Chemistry, vol. 20B, Mar. 1981, pp. 234-237.*
Wuts, G.M., Greene's Protective Groups in Organic Synthesis, Fourth Edition, 2006, John Wiley and Sons, Chapter 7, Protection for the Amino Group, pp. 696-926.*
U.S. Appl. No. 13/638,484, filed Aug. 30, 2012, Bailly, et al.
U.S. Appl. No. 13/638,500, filed Sep. 28, 2012, Priem, et al.
U.S. Appl. No. 13/628,867, filed Sep. 27, 2012, Bon, et al.
U.S. Appl. No. 13/711,891, filed Dec. 12, 2012, Friesz.
U.S. Appl. No. 13/742,810, filed Jan. 16, 2013, Bailly, et al.
U.S. Appl. No. 13/742,816, filed Jan. 16, 2013, Bailly, et al.
International Search Report for WO2012/010913 dated Jan. 26, 2012.

* cited by examiner

Primary Examiner — Andrew D Kosar
Assistant Examiner — John Mauro
(74) Attorney, Agent, or Firm — Kelly L. Bender

(57) ABSTRACT

The subject of the invention is a novel process for the preparation of N-[2-n-butyl-3-{4-[(3-di-n-butylamino)-propoxy]benzoyl}benzofuran-5-yl]-methanesulfonamide of formula I:

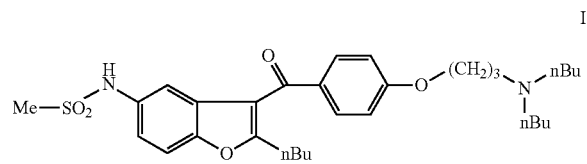

and pharmaceutically acceptable salts thereof wherein the acyl group of the benzofuran derivative of the general formula II:

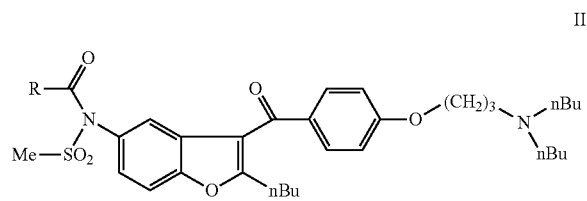

where R represents $C_{1-4}$ alkyl-, $C_{1-4}$ alkoxy- or aryl group, is selectively cleaved and if desired, the resulting compound of formula I is transformed into its salt.

16 Claims, No Drawings

PROCESS FOR THE PREPARATION OF DRONEDARONE

This application is a continuation of International Application No. PCT/HU2011//000067, filed Jul. 13, 2011, which is incorporated herein by reference, and which claims the benefit of priority of Hungarian Application No. P1000386, filed Jul. 22, 2010.

This invention relates to a novel process for the preparation of N-[2-n-butyl-3-{4-[(3-di-n-butylamino)propoxy]benzoyl}-1-benzofuran-5-yl]-methanesulfonamide (dronedarone) of formula I

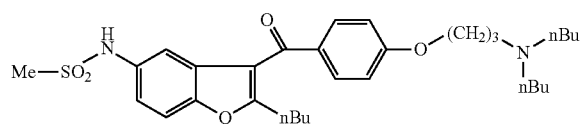

and its pharmaceutically acceptable salts, as well as to the new intermediates of the preparation process.

Dronedarone of the formula I is useful in the treatment of certain pathological changes of the cardiovascular system, first of all in the treatment of angina pectoris, high blood pressure, arrhythmia and insufficient cerebral blood flow (EP 0471609 B1).

Presently several methods for the preparation of Dronedarone of formula I are known. In one of the prior art methods (EP 0471609 B1) the 2-n-butyl-5-nitro-benzofuran of formula VIII

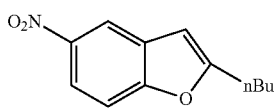

is reacted with anisoyl chloride under Friedel-Crafts conditions, the resulting

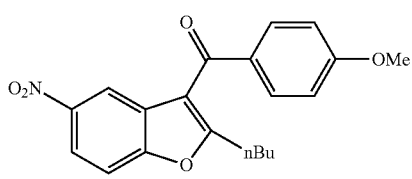

2-n-butyl-3-(4-methoxy-benzoyl)-5-nitro-benzofuran of formula IX is then heated in the presence of aluminum chloride,

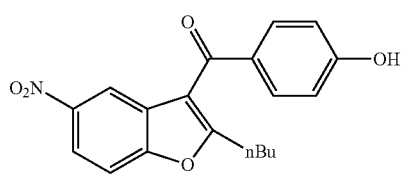

to obtain the 2-n-butyl-3-(4-hydroxy-benzoyl)-5-nitro-benzofuran of formula X.

Utilization of this reaction step in industrial scale, however, involves difficulties, because the compound of formula IX is mutagenic, and aluminum chloride is harmful to the health. Reaction of the resulting compound of formula X with di-n-butylamino-propyl chloride gives the 2-n-butyl-3-[4-(3-di-n-butylamino-propoxy)-benzoyl]-5-nitro-benzofuran of formula XI,

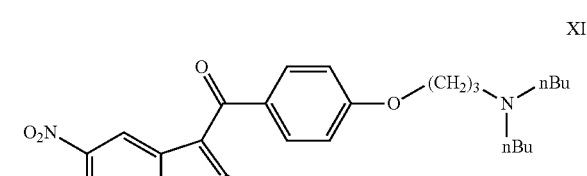

which on reduction with platinum oxide catalyst gives the

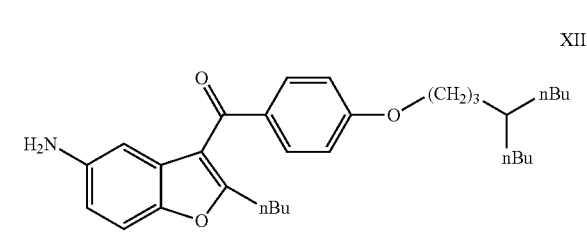

5-amino-2-n-butyl-3-[4-(3-di-n-butylamino-propoxy)benzoyl]benzofuran of formula XII. Finally, mesylation of the compound of formula XII leads to dronedarone of formula I.

This is a linear synthesis, where the parts of the desired molecule are built up stepwise, using more and more complicated molecules in the consecutive steps, which is economically unfavourable.

In the last step, the selective mesylation of the amino group of the compound of formula XII does not take place easily, therefore the double mesylated derivative also appears beside dronedarone of formula I. According to the literature, this process, after purification by column chromatography, furnishes dronedarone in 61.6% yield, but the process is complicated, not suitable for industrial application.

Another process for the preparation of dronedarone is described in patent application of publication number WO 02/48132. This super-convergent route [Process C] consists of the following steps:

The 5-amino-2-n-butyl-benzofuran of formula XIII

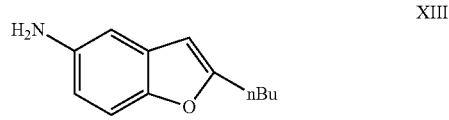

is mesylated and the resulting 2-n-butyl-5-methylsulfonamido-benzofuran of formula V

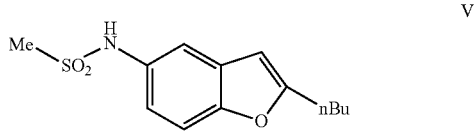

is reacted under Friedel-Crafts conditions with the hydrochloride salt of the 4-[3-(di-n-butylamino)propoxy]benzoyl chloride of formula IV

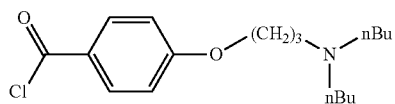

IV to obtain the hydrochloride salt of dronedarone of formula I.

In this method the sequence of the reaction steps is changed, the reduction and the mesylation steps are at the beginning of the synthesis.

The process disclosed in WO 02/48132 (process C) is simpler and more economical taken into consideration the number of the reaction steps. Unfortunately, in the last reaction step rather impure dronedarone.HCl is formed which is the obvious consequence of the presence of dibutylamino group in the Friedel-Crafts reaction. According to Examples 3 and 4, the crude dronedarone hydrochloric acid is be prepared with a yield of 90% which was further purified and finally the crude dronedarone base was produced with a yield of 86%. This base is reacted with hydrochloric gas dissolved in isopropanol which results in pure dronedarone hydrochloric salt. No yield was given for this reaction step. According to example 5 crude dronedarone hydrochloric salt dissolved in dichloromethane was prepared with a yield of 90%, which was washed with water and reacted with hydrochloric acid gas dissolved in isopropanol, resulting dronedarone hydrochloric acid salt again. The quality of this product is not known.

Another drawback of the method is that the reactants used in the Friedel-Crafts reaction and the obtained by-products are insoluble in water, thus they cannot be removed from the system by aqueous washing.

Our aim was to work out a novel method for the preparation of dronedarone and its pharmaceutically acceptable salts, which method avoids the above mentioned disadvantages and is economical and industrially applicable.

We have found that if the acyl group of the benzofuran derivative of formula II—where R represents $C_{1-4}$ alkyl-, $C_{1-4}$ alkoxy- or aryl group-,

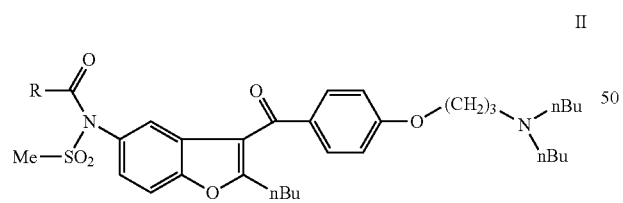

II is selectively cleaved, then dronedarone of formula I is obtained in good yield and in appropriate purity.

According to our invention the cleavage of the acyl group from the compound of formula II—where the meaning of R is as defined above—is performed in an alcoholic solvent or in the mixture of alcoholic solvents, in the presence of an alkali alcoholate, alkali hydroxide or an inorganic acid. As for alcoholic solvent methanol, ethanol or their mixture is applied. As for alkali alcoholate sodium- or potassium methylate, or sodium- or potassium ethylate is applied. As for alkali hydroxide sodium- or potassium hydroxide is applied. As for inorganic acid hydrochloric acid or sulfuric acid is applied.

The reaction is carried out at a temperature between 20° C. and the boiling point of the solvent or the solvent mixture.

When carrying out the process according to our invention, a/1) the 2-n-butyl-5-methylsulfonamido-benzofuran of formula V

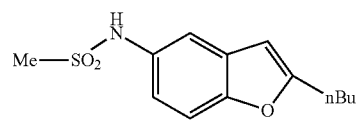

V is acylated with an acid halide of the general formula VI

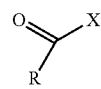

VI where R stands for $C_{1-4}$ alkyl-, $C_{1-4}$ alkoxy- or aryl group, X means halogen atom-, or a/2) a compound of the general formula VII

VII where R stands for $C_{1-4}$ alkyl-, $C_{1-4}$ alkoxy- or aryl group- is mesylated, and b) the thus obtained compound of the general formula III

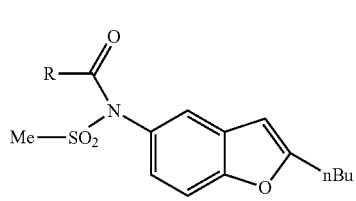

III where the meaning of R is as defined above—is reacted with the hydrochloride of the 4-(3-di-n-butylamino-propoxy)benzoyl chloride of formula IV,

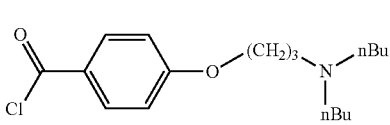

IV and c) from the resulting benzofuran derivative of the general formula II

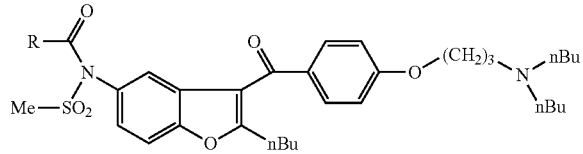

where the meaning of R is as defined above—, the acyl group is selectively cleaved by the method described above.

The Meanings of the Above Mentioned Substituents are:

By $C_{1-4}$ alkyl group we mean a saturated, straight or branched aliphatic group consisting of 1-4 carbon atoms, such as methyl-, ethyl-, propyl-, isopropyl-, butyl-, isobutyl-, secondary-butyl-, tertiary-butyl group.

By $C_{1-4}$ alkoxy group we mean —O—($C_{1-4}$ alkyl group)— where the meaning of the $C_{1-4}$ alkyl group is defined above—, such as methoxy-, ethoxy-, propoxy-, isopropoxy-, butoxy-, isobutoxy-, secondary-butoxy- or tertiary-butoxy group.

By halogen atom we mean chloro, fluoro, iodo or bromo atom.

By aryl group we mean phenyl or naphthyl group, which optionally may be mono- or multi-substituted with $C_{1-4}$ alkyl-, $C_{1-4}$ alkoxy- group and with halogen atom.

According to our invention the reaction of 2-n-butyl-5-methylsulfonamido-benzofuran of formula V

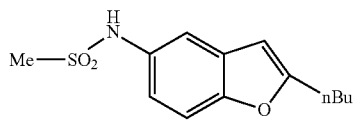

with the compound of the general formula VI

where the meanings of R and X are as defined above—is carried out in an inert organic solvent or in the mixture of inert organic solvents. As for inert organic solvent, halogenated organic solvents (dichloromethane, dichloroethane, chlorobenzene) may be applied. The reaction of the compounds of the general formulae V and VI is carried out in the presence of an acid binder. As for acid binder, tertiary amines (trialkylamine or pyridine) can be applied.

The mesylation reaction of the compound of the general formula VII

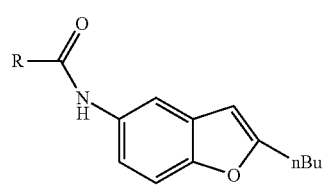

where the meaning of R is defined above—is carried out in the presence of an inert organic solvent or mixture of inert organic solvents. As for inert organic solvent, halogenated organic solvents (dichloromethane, dichloroethane, chlorobenzene) are applied.

The mesylation reaction of the compound of the general formula VII—where the meaning of R is defined above—is carried out in the presence of an acid binder. As for acid binder, tertiary amines (trialkylamine or pyridine) are applied.

The reaction of a compound of the general formula III

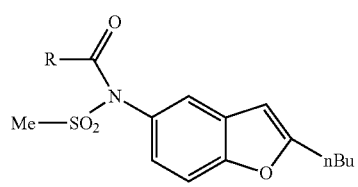

where the meaning of R is defined above—with the hydrochloride of the compound of formula IV

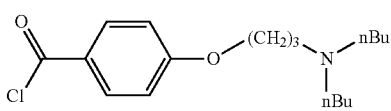

is performed in an inert organic solvent or in the mixture of inert organic solvents. As for inert organic solvent, halogenated organic solvents (dichloromethane, dichloroethane, chlorobenzene) are applied.

The reaction of a compound of the general formula III and the compound of formula IV is carried out in the presence of a Lewis-acid (iron(III) chloride or aluminum chloride). The Lewis-acid is applied in an amount of maximum 5 equivalents.

The hydrochloride of the 4-(3-di-n-butylamino-propoxy) benzoyl chloride of formula IV

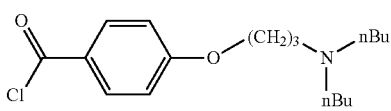

and its preparation is known from the literature (EP 0471609 B1).

The 2-n-butyl-5-methylsulfonamido-benzofuran of formula V

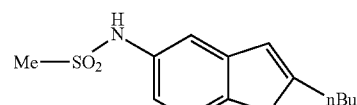

and its preparation is known from the literature (WO 02/048132).

The compound of the general formula VII

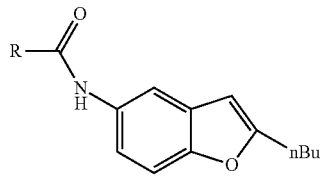

where R stands for methyl group—and its preparation is known from the literature (WO03/040120).
The compounds of the general formula II

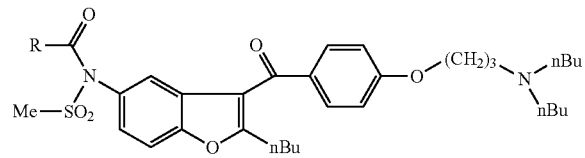

where R stands for $C_{1-4}$ alkyl, $C_{1-4}$ alkoxy or aryl group—, the compounds of the general formula III

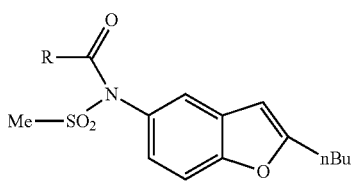

where R stands for $C_{1-4}$ alkyl, $C_{1-4}$ alkoxy or aryl group—, and
the compounds of the general formula VII

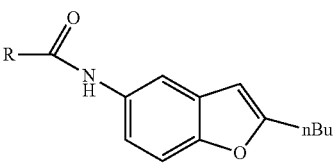

where R stands for $C_{2-4}$ alkyl, $C_{1-4}$ alkoxy or aryl group— are new compounds, not described in the literature.

Further details of the invention are demonstrated by the following examples, but the Applicant is not limiting the claims to the examples.

EXAMPLE 1

N-[2-n-butyl-3-[4-[-3(-di-n-butylamino)propoxy] benzoyl]-1-benzofuran-5-yl]-methanesulfonamide
(I)

2 g of N-[2-n-butyl-3-[4-[3 (-di-n-butylamino)propoxy] benzoyl]-1-benzofuran-5-yl]-N'-acetyl-methanesulfonamide (the compound of the general formula II, where R represents methyl group) is dissolved in 20 ml of methanol. After complete dissolution, 1.05 g of sodium methylate is added, the reaction mixture is heated to 60° C. and stirred at that temperature for 2 hours. The mixture is cooled to room temperature and the solvent is removed by evaporation. The residue is dissolved in 95 ml of dichloromethane and washed with 2×30 ml of water.

After evaporation 1.74 g (94%) raw product is obtained.

Purity (HPLC): 95.7%.

The raw product is purified through its oxalate salt.

Purity of the liberated dronedarone base: 100%.

$^1$H NMR (DMSO): 0.8-0.9 (m, 9H); 1.2-1.5 (m, 10H); 1.67 (5', 2H); 1.87 (5', 2H); 2.38 (t, J=7.2 Hz, 4H); 2.57 (m, 2H); 2.81 (t, J=7.5 Hz, 2H); 2.91 (s, 3H); 4.15 (t, J=6.2 Hz, 2H); 7.09 (d, J=8.8 Hz, 2H); 7.24 (dd, J=8.9, 2.2 Hz, 1H); 7.34 (d, J=2.1 Hz, 1H); 7.65 (d, J=8.8 Hz, 1H); 7.81 (d, J=8.8 Hz, 2H).

EXAMPLE 2

N-[2-n-butyl-3-[4-[-3(-di-n-butylamino)propoxy] benzoyl]-1-benzofuran-5-yl]-methanesulfonamide
(I)

2 g of N-[2-n-butyl-3-[4-[3 (-di-n-butylamino)propoxy] benzoyl]-1-benzofuran-5 -yl]-N'-ethoxycarbonyl-methanesulfonamide (the compound of the general formula II, where R represents ethoxy group) is dissolved in 20 ml of methanol. After complete dissolution 0.89 g of sodium hydroxide is added, the reaction mixture is heated to 65° C., stirred at that temperature for 2 hours, then cooled to room temperature and the solvent is removed by evaporation. The residue is dissolved in 30 ml of dichloromethane and washed with 2×25 ml of water. The solvent is removed by evaporation.

Mass of the raw product: 1.68 g (94.8%).

Purity (HPLC): 96.7%.

The raw product is purified through its oxalate salt.

Purity of the liberated dronedarone base: 100%.

The product is identical with that obtained in Example 1.

EXAMPLE 3

N-[2-n-butyl-3-[4-[-3(-di-n-butylamino)propoxy] benzoyl]-1-benzofuran-5-yl]-methanesulfonamide
(I)

2.5 g of N-[2-n-butyl-3-[4-[3 (-di-n-butylamino)propoxyl] benzoyl]-1 -benzofuran-5 -yl]-N'-benzoyl-methanesulfonamide (the compound of the general formula II where R represents phenyl group) is dissolved in the mixture of 20 ml of methanol and 1.15 ml of hydrochloric acid (37%). The reaction mixture is heated to 55-60° C., stirred at that temperature for 3 hours, then cooled to room temperature and the solvent is removed by evaporation. The residue is dissolved in 25 ml of dichloromethane, and then 20 ml of water is added to it. The pH of the mixture is adjusted to 7 and the phases are separated. The dichloromethane phase is washed with 2×20 ml of 5% sodium carbonate solution, then with 2×20 ml of water. The solvent is removed by evaporation.

Mass of the raw product: 2.02 g (95.8%).

The raw product is purified through its oxalate salt.

Purity of the oxalate salt: 100%.

The product is identical with that obtained in Example 1.

EXAMPLE 4

N-[2-n-butyl-3-[4-[-3 (-di-n-butylamino)propoxy] benzoyl]-1-benzofuran-5-yl]-methanesulfonamide (I)

The procedure as described in Example 1. is followed, with the difference that potassium methylate is used, instead of sodium methylate.
Yield: 94.5%.
Purity (HPLC): 96.4%.

EXAMPLE 5

N-[2-n-butyl-3-[4-[-3(-di-n-butylamino)propoxy] benzoyl]-1-benzofuran-5-yl]-methanesulfonamide (I)

The procedure as described in Example 3. is followed, with the difference that instead of hydrochloric acid solution, potassium hydroxide in methanol as solvent is used.
Yield: 94.7%.
Purity (HPLC): 95.9%.

EXAMPLE 6

N-[2-n-butyl-3-[4-[-3-(di-n-butylamino)propoxy] benzoyl]-1-benzofuran-5-yl]-N'-acetyl-methanesulfonamide (Compound of the General Formula II, Where R Represents Methyl Group)

2 g of N-acetyl-N'-(2-n-butyl-1-benzofuran-5-yl)-methanesulfonamide (compound of the general formula III, where R represents methyl group) is dissolved in 12 ml of dichloromethane and 2.4 g of 4-(di-n-butylamino-propoxy)benzoyl chloride hydrochloride (IV) is added to the solution. The reaction mixture is cooled to 5° C. and in four portions, during 15 minutes 0.98 g iron(III) chloride is added. The reaction mixture is warmed to 20° C., stirred at that temperature for 1 hour, then warmed to 35-40° C. and 16 ml of water is added to it. After 30 minutes of stirring the phases are separated. The dichloromethane phase is washed at 35-40° C. with 7 ml of water, 2×7 ml of 5% sodium hydrogen carbonate solution, then again with 2×7 ml of water, and then it is evaporated.
Mass of the raw product: 3.78 g (97.6%).
Purity (HPLC): 92.5%.
$^1$H NMR (DMSO): 7.83 (d, J=8.8 Hz, 2H); 7.81(d, J=8.7 Hz, 1H); 7.54(d, J=2.2 Hz, 1H); 7.47 (dd, J=2.2, 8.7 Hz, 1H); 7.09 (d, J=8.8 Hz, 2H); 4,15 (t, J=6.0 Hz, 2H); 3.54 (s, 3H); 2.83 (t, J=7.5 Hz, 2H); 2,.4 (m, 2H); 2.37 (t, J=7.1 Hz, 4H); 1.93 (s, 3H); 1.87 (5', J=6.6 Hz, 2H); 1.70 (5', J=7.5 Hz, 2H); 1.37 (m, 4H); 1.8 (m, 6H); 0.86 (t, J=7.2 Hz, 6H); 0.84 (t, J=7.3 Hz, 3H).
Molar mass [M+H]$^+$ calculated=599,3155 Da
[M+H]$^+$ measured=599,3157 Da

EXAMPLE 7

N-[2-n-butyl-3-[4-[-3-(di-n-butylamino)propoxy] benzoyl]-1-benzofuran-5-yl]-N'-ethoxycarbonyl-methanesulfonamide (Compound of the General Formula II, Where R Represents Ethoxy Group)

2 g of N-ethoxy-N'-(2-n-butyl-1-benzofuran-5-yl)-methanesulfonamide (compound of the general formula III, where R represents ethoxy group) is dissolved in 12 ml of dichloromethane and 2.3 g of the hydrochloride of 4-(di-n-butylamino-propoxy)benzoyl chloride (IV) is added to the solution. The reaction mixture is cooled to 5° C. and in four portions, in a period of 15 minutes 1.0 g iron(III) chloride is added. The reaction mixture is warmed to 20° C., stirred at that temperature for 1 hour, warmed to 35-40° C. and 16 ml of water is added to it. After 30 minutes of stirring the phases are separated. The dichloromethane phase is washed at 35-40° C. with 7 ml of water, 2×7 ml of 5% sodium hydrogen carbonate solution, and again with 2×7 ml of water, then evaporated.
Mass of the raw product: 3.7 g (95.1%).
Purity (HPLC): 93.7%.
$^1$H NMR (DMSO): 7.82 (d, J=8.8 Hz, 2H); 7.74 (d, J=8.7 Hz, 1H); 7.46 (d, J=2.2 Hz, 1H); 7.38 (dd, J=2.3, 8.7 Hz, 1H); 7.09 (d, J=8.8 Hz, 2H); 4.21 (q, J=7.2 Hz, 2H); 4.15 (t, J=6.1 Hz, 2H); 3.59 (s, 3H); 2.81 (t, J=7.6 Hz, 2H); 2.53 (m, 2H); 2.37 (t, J=7.2 Hz, 4H); 1.87 (5', J=6.5 Hz, 2H); 1.70 (5', J=7.4 Hz, 2H); 1.36 (m, J=6.5 Hz, 4H); 1.27 (m, 6H); 1.18 (t, J=7.0 Hz, 3H); 0.85 (t, J=7.3 Hz, 6H) 0.83 (d, J=7.3 Hz, 3H).
Molar mass [M+H]$^1$ calculated=629,3260 Da
[M+H]$^+$ measured=629,3251 Da

EXAMPLE 8

N-[2-n-butyl-3-[4-[-3-(di-n-butylamino)propoxy] benzoyl]-1-benzofuran-5-yl]-N'-benzoyl-methanesulfonamide (Compound of the General Formula II, Where R Represents Phenyl Group)

2.5 g of N-benzoyl-N'-(2-n-butyl-1-benzofuran-5-yl)-methanesulfonamide (compound of the general formula III, where R represents phenyl group) is dissolved in 16 ml of dichloromethane and 2.5 g of the hydrochloride of 4-(di-n-butylamino-propoxy)benzoyl chloride (IV) is added to the solution. The reaction mixture is cooled to 5° C. and in four portions, in a period of 15 minutes 0.9 g aluminum chloride is added. The reaction mixture is warmed to 35-40° C. and 20 ml of water is added to it. After 30 minutes of stirring the phases are separated. The dichloromethane phase is washed at 35-40° C. with 10 ml of water, 2×10 ml of 5% sodium hydrogen carbonate solution, then again with 2×10 ml of water, then evaporated.
Mass of the raw product: 4.42 g (99%).
Purity (HPLC): 94.5%.
Molar mass [M+H]$^+$ calculated=661,3311 Da
[M+H]$^+$ measured=661,3310 Da

EXAMPLE 9

N-[-2-n-butyl-3-[4-[-3-(di-n-butylamino)propoxy] benzoyl]-1-benzofuran-5 -yl]-N'-ethoxycarbonyl-methanesulfonamide (Compound of the General Formula II, where R Represents Ethoxy Group)

The procedure as described in Example 7. is followed, with the difference that chlorobenzene is used as solvent, instead of dichloromethane, and aluminum chloride is used as Lewis acid, instead of iron(III) chloride.
Yield: 93.7%.
Purity (HPLC): 95.7%.

EXAMPLE 10

N-acetyl-N'-(2-n-butyl-1-benzofuran-5-yl)-methanesulfonamide (Compound of the General Formula III, Where R Represents Methyl Group)

10 g of (2-n-butyl-benzofuran-5-yl)-methanesulfonamide (V) is dissolved in 50 ml dichloromethane. The reaction mixture is cooled to 10° C. and 5.5 g of pyridine is added. To the resulting clear solution 5.73 g of acetyl chloride (compound of the general formula VI, where R represents methyl group, X represents chloro atom) is added at 10° C., in a period of 30 minutes, and the mixture is stirred at that temperature for 1 hour. The reaction mixture is allowed to warm to room temperature and stirred for 4 hours. The dichloromethane suspension is washed with 2×100 ml water, the phases are separated and the dichloromethane phase is evaporated.

Mass of the raw product: 12.9 g.
Purity (HPLC): 98%.
$^1$H NMR (DMSO-d 6): 7.68 (d, J=2.1 Hz, 1H); 7.64 (d, J=8.6 Hz, 1H); 7.32 (dd, J=8.5 Hz; 2.2 Hz, 1H); 6.7 (s, 1H); 3.57 (s, 3H); 2.84 (t, J=7.5 Hz, 2H); 1.93 (s, 3H); 1.72 (5', J=7.5 Hz, 2H); 1.42 (6', J=7.5 Hz, 2H); 0.96 (t, J=7.6 Hz, 6H).
Molar mass [M+H]$^+$ calculated=310,1113 Da
[M+H]$^+$ measured=310,1096 Da

EXAMPLE 11

N-ethoxycarbonyl-N'-(2-n-butyl-1-benzofuran-5-yl)-methanesulfonamide (Compound of the General Formula III, Where R Represents Ethoxy Group)

5 g of (2-n-butyl-benzofuran-5-yl)-methanesulfonamide is dissolved in 38 ml of dichloromethane. The reaction mixture is cooled to 10° C. and 4.0 g of pyridine is added. To the resulting clear solution 5.38 g of ethyl chloroformate (compound of the general formula VI, where R represents ethoxy group, X represents chloro atom) is added at 10° C., in a period of 30 minutes. The mixture is stirred at that temperature for 1 hour, then allowed to warm to room temperature and stirred at room temperature for 2 hours. The dichloromethane suspension is washed with 2×50 ml of water, 1×50 ml of 5% sodium hydrogen carbonate solution, then again with 1×50 ml of water, and evaporated.

Mass of the residue: 6 g.
To this residue 15 ml of isopropanol is added and the mixture is heated to reflux temperature. From the resulting clear solution white crystalline material precipitates upon cooling.

Mass of the raw product: 5.3 g (84%).
Melting point: 97.2° C.
Purity (HPLC): 100%.
$^1$H NMR (DMSO-d 6): 7.58 (d, J=1.9 Hz, 1H); 7.57 (d, J=9.0 Hz, 1H); 7.22 (dd, J=8.5 Hz, 2.2 Hz, 1H); 6.67 (d, J=0.3 Hz, 1H); 4.22 (q, J=7.1 Hz, 2H); 3.61 (s, 3H); 2.83 (t, J=7.4 Hz, 2H); 1.72 (5', J=7.5 Hz, 2H); 1.41 (6', J=7.5 Hz, 4H); 1.17 (t, J=7.1 Hz, 3H); 0.96 (t, J=7.4 Hz, 3H).
Molar mass [M+H]$^+$ calculated=340,1219 Da
[M+H]$^+$ measured=340,1216 Da

EXAMPLE 12

N-benzoyl-N'-(2-n-butyl-1-benzofuran-5-yl)-methanesulfonamide (Compound of the General Formula III, Where R Represents Phenyl Group)

2 g of (2-n-butyl-benzofuran-5-yl)-methanesulfonamide (V) is dissolved in 15 ml of dichloromethane. The reaction mixture is cooled to 10° C. and 1.1 g of pyridine is added, then at 10° C., in a period of 30 minutes 1.96 g of benzoyl chloride (compound of the general formula VI, where R represents phenyl group, X represents chloro atom) is added and the mixture is stirred at that temperature for 5.5 hours. The reaction mixture is washed with 2×20 ml of water, 1×20 ml of 5% sodium hydrogen carbonate solution, again with 1×20 ml of water and evaporated.

Mass of the raw product: 2.8 g (100%).
Purity (HPLC): 98%.
$^1$H NMR (DMSO-d 6): 7.63 (d, J=1.7 Hz, 1H); 7.57 (d, J=7.3 Hz, 2H); 7.47 (d, J=8.6 Hz, 1H); 7.37 (t,J=7.1 Hz, 1H); 7.3 (m, 3H); 6.60 (s, 1H); 3.59 (s, 3H); 2.76 (t, J=7.5 Hz, 2H); 1.66 (5', J=7.4 Hz, 2H); 1.37 (5', J=7.4 Hz, 2H); 0.92 (t, J=7.4 Hz, 3H).
Molar mass [M+H]$^+$ calculated=372,1270 Da
[M+H]$^+$ measured=372,1281 Da

EXAMPLE 13

N-acetyl-N'-(2-n-butyl-1-benzofuran-5-yl)-methanesulfonamide (Compound of the General Formula III, Where R Represents Methyl Group)

2 g of (2-n-butyl-benzofuran-5-yl)-acetamide (compound of the general formula VII, where R represents methyl group) is dissolved in 20 ml of dichloromethane. The reaction mixture is heated to 30-35° C. and at first during 15 minutes 0.76 mg of pyridine, then during 30 minutes 1.1 g of methanesulfonyl chloride are added. The reaction mixture is stirred at 30-35° C. for 5 hours, then washed with 1×15 ml of water, 1×15 ml of 5% hydrochloric acid solution, and again with 1×15 ml of water, then evaporated.

Mass of the product: 2.2 g (82.9%).
Purity (HPLC): 92.1%.
The product is identical with that obtained according to Example 10.

EXAMPLE 14

N-ethoxycarbonyl-N'-(2-n-butyl-1-benzofuran-5-yl)-methanesulfonamide (Compound of the General Formula III, Where R Represents Ethoxy Group)

2.2 g of (2-n-butyl-benzofuran-5-yl)ethoxycarbonylamide (compound of the general formula VII, where R represents ethoxy group) is dissolved in 20 ml of dichloromethane. The reaction mixture is heated to 30-35° C. and at first during 15 minutes 0.83 mg of pyridine, and then during 30 minutes 1.3 g of methanesulfonyl chloride is added. The reaction mixture is stirred at that temperature for 4.5 hours, and then it is washed with 1×15 ml of water, 1×15 ml of 5% hydrochloric acid solution, again with 1×15 ml of water, and then evaporated.

Mass of the product: 2.4 g (84.2%)
The product is recrystallized from 15 ml of isopropanol.
Yield: 82.7%.
The product is identical with the compound obtained according to Example 11.

EXAMPLE 15

N-benzoyl-N'-(2-n-butyl-1-benzofuran-5-yl)-methanesulfonamide (Compound of the General Formula III, Where R Represents Phenyl Group)

1.8 g of 2-(2-n-butyl-benzofuran-5-yl)-benzamide (compound of the general formula VII, where R represents phenyl group) is dissolved in 19 ml of dichloromethane. The reaction mixture is heated to 30-35° C. and at first during 15 minutes 0.53 mg of pyridine, and then during 30 minutes 0.78 g of methanesulfonyl chloride is added.

The reaction mixture is stirred at 30-35° C. for 6 hours, then washed with 1×15 ml of water, 1×15 ml of 5% hydrochloric acid solution, and again with 1×15 ml of water, then evaporated.

Mass of the product: 2.1 g (92%).
Purity (HPLC): 94.7%.
The product is identical with the compound obtained according to Example 12.

EXAMPLE 16

N-benzoyl-N'-(2-n-butyl-1-benzofuran-5-yl)-methanesulfonamide (Compound of the General Formula III, Where R Represents Phenyl Group)

The procedure as described in Example 15. is followed, with the difference that triethylamine is used, instead of pyridine.
Yield: 92.9%.
Purity (HPLC): 95.2%.
The product is identical with the compound obtained according to Example 15.

EXAMPLE 17

2-n-butyl-benzofuran-5-yl)ethoxycarbonylamide (Compound of the General Formula VII, Where R Represents Ethoxy Group)

1 g of 5-amino-2-n-butyl-benzofuran is dissolved in 10 ml of dichloromethane and at first 0.46 g pyridine dissolved in 1 ml of dichloromethane is added dropwise in 5 minutes at room temperature, then 0.63 g of ethyl chloroformate in 1 ml of dichloromethane in 30 minutes at room temperature. The dichloromethane solution is washed with 1×15 ml of water, 1×15 ml of 5% sodium hydrocarbonate solution, 1×15 ml of water, 1×15 ml of 5% hydrochloric acid solution and 1×15 ml of water, and then it was evaporated.

Mass of the product: 1.0 g (73%). It crystallizes while standing.
Purity (HPLC): 98.1%
Melting point: 59.9-60.7° C.
$^1$HNMR (DMSO) 0.91 (t, J=7.32 Hz, 3H); 1.25 (t, J=7.10 Hz, 3H); 1.35 (sxt, J=7.42 Hz, 2H); 1.65 (quin, J=7.50 Hz, 2H); 2.72 (t, J=7.55 Hz, 2H); 4.12 (q, J=7.10 Hz, 2H); 6.52 (s, 1H); 7.24 (dd, J=8.70 Hz, 1H); 7.37 (d, J=8.70, 1.37 Hz, 1H); 7.67 (br.s.1H).

EXAMPLE 18

2-(2-n-butyl-benzofuran-5-yl)benzamide (Compound of the General Formula VII, Where R Represents Phenyl Group)

1 g of 5-amino-2-n-butyl-benzofuran is dissolved in 10 ml of dichloromethane and at first 0.46 g pyridine dissolved in 1 ml of dichloromethane is added dropwise in 5 minutes at room temperature, then 0.98 g of benzoyl chloride is added in 1 ml of dichloromethane in 30 minutes at room temperature. The dichloromethane solution is washed with 1×15 ml of water, with 1×15 ml of 5% sodium hydrocarbonate solution with 1×15 ml of water with 1×15 ml of 5% hydrochloric acid solution and with 1×15 ml of water, and then it was evaporated.

Mass of the product: 1.39 g (89.6%)
Purity (HPLC): 97.5%
Melting point: 116.6-118.0° C.
$^1$HNMR (DMSO) 0.92 (t, J=7.32 Hz, 3H); 1.38 (sxt, J=7.42 Hz, 2H); 1.68 (quin, J=7.50 Hz, 2H); 2.76 (t, J=7.55 Hz, 2H); 6.60 (s, 1H); 7.46 (d, J=8.70 Hz, 1H); 7.51-7.56 (m, 3H); 7.59 (tt, J=7.32, 2.00 Hz, 1H); 7.98 (d, J=7.10 Hz, 2H); 8.02 (d, J=1.83 Hz, 1H).

What is claimed is:

1. A process for the preparation of N-[2-n-butyl-3-{4-[(3-di-n-butylamino)-propoxy]benzoyl}benzofuran-5-yl]-methanesulfonamide of formula I:

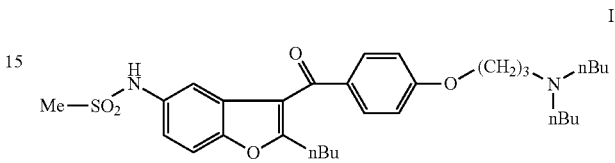

or a pharmaceutically acceptable salt thereof; comprising selectively removing the C(O)—R group of the benzofuran derivative of formula II:

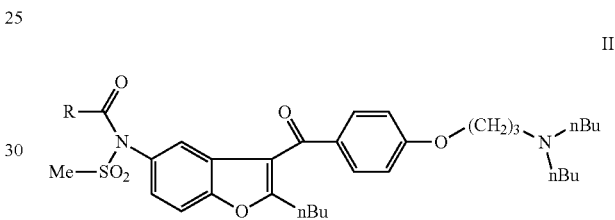

where R represents $C_{1-4}$ alkyl-, $C_{1-4}$ alkoxy- or aryl group, and if desired, transforming the resulting compound of formula I into its salt.

2. The process according to claim 1, comprising carrying out the removal of the C(O)—R group in an alcoholic organic solvent or in a mixture of alcoholic organic solvents.

3. The process according to claim 1, comprising carrying out the removal of the C(O)—R group in the presence of an alkali alcoholate.

4. The process according to claim 1, comprising carrying out the removal of the C(O)—R group in the presence of an alkali metal- or alkali earth metal hydroxide.

5. The process according to claim 1, comprising carrying out the removal of the C(O)—R group in the presence of an inorganic acid.

6. The process according to claim 1, comprising carrying out the removal of the C(O)—R group in a solvent or solvent mixture at a temperature between 20° C. and the boiling point of the applied solvent or solvent mixture.

7. The process according to claim 1, comprising
a) reacting the 2-n-butyl-5-methylsulfonamido-benzofuran of formula V:

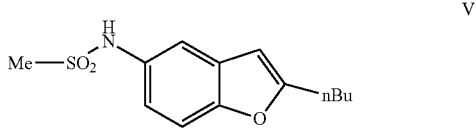

with an acid halide of formula VI:

VI where R represents $C_{1-4}$ alkyl-, $C_{1-4}$ alkoxy- or aryl group, and X represents halogen atom, and b) reacting the thus obtained compound of the general formula III:

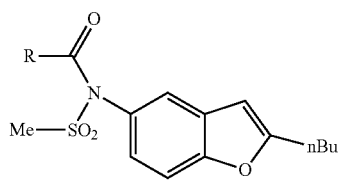

III where R represents $C_{1-4}$ alkyl-, $C_{1-4}$ alkoxy- or aryl group, in the presence of a Lewis-acid with the hydrochloride of the 4-(3-di-n-butylamino-propoxy)benzoyl chloride of formula IV:

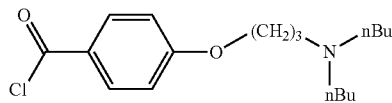

IV and b) selectively removing the C(O)—R group from the resulting benzofuran derivative of formula II:

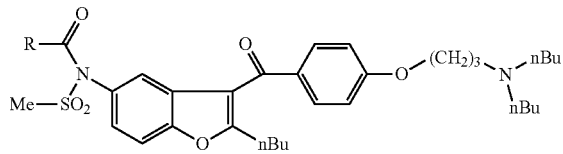

II where R represents $C_{1-4}$ alkyl-, $C_{1-4}$ alkoxy- or aryl group, and if desired, transforming the thus obtained compound of formula I is into its salt.

8. The process according to claim 7, comprising carrying out the reaction in step a) in an inert organic solvent or in a mixture of inert organic solvents.

9. The process according to claim 7, comprising carrying out the reaction in step a) in the presence of an acid binder.

10. The process according to claim 7, comprising carrying out the reaction in step b) in an inert organic solvent or in a mixture of inert organic solvents.

11. The process according to claim 1, comprising a) mesylating a compound of formula VII:

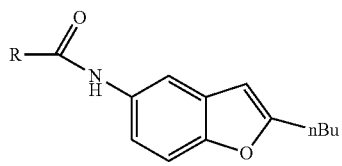

VII where R represents $C_{1-4}$ alkyl-, $C_{1-4}$ alkoxy- or aryl group, and b) reacting the resulting compound of formula III:

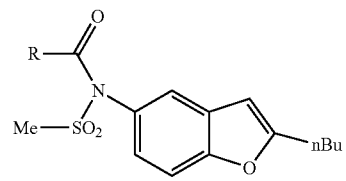

III where R represents $C_{1-4}$ alkyl-, $C_{1-4}$ alkoxy- or aryl group, in the presence of a Lewis-acid with the hydrochloride of the 4-(3-di-n-butylamino-propoxy)benzoyl chloride of formula IV:

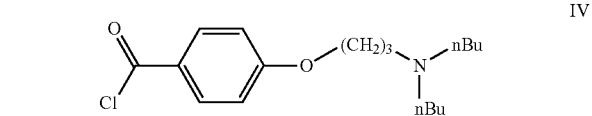

IV and c) selectively removing the C(O)—R group from the thus obtained benzofuran derivative of formula II:

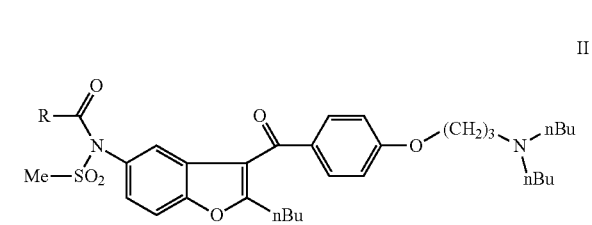

II where R represents $C_{1-4}$ alkyl-, $C_{1-4}$ alkoxy- or aryl group, and if desired, transforming the resulting compound of formula I into its salt.

12. The process according to claim 11, comprising carrying out the reaction in step a) in an inert organic solvent or in a mixture of inert organic solvents.

13. The process according to claim 11, comprising carrying out the reaction in step a) in the presence of an acid binder.

14. The process according to claim 11, comprising carrying out the reaction in step b) an inert organic solvent or in a mixture of inert organic solvents.

15. A compound of formula II:
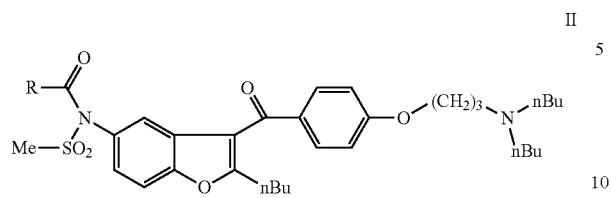
where R represents $C_{1-4}$ alkyl-, $C_{1-4}$ alkoxy- or aryl group.
16. The compound of formula III:
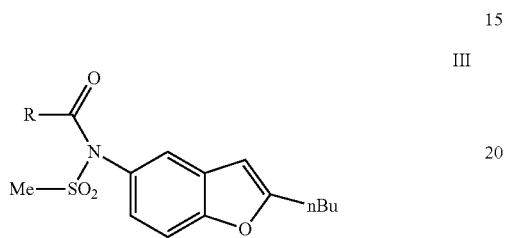
where R represents $C_{1-4}$ alkyl-, $C_{1-4}$ alkoxy- or aryl group.
* * * * *